(12) United States Patent
Ramsey

(10) Patent No.: US 11,298,005 B2
(45) Date of Patent: *Apr. 12, 2022

(54) INSTRUMENT TIP PROTECTOR

(71) Applicant: MEDITECH ENDOSCOPY LTD, Chesterfield (GB)

(72) Inventor: Peter Ramsey, Chesterfield (GB)

(73) Assignee: MEDITECH ENDOSCOPY LTD, Chesterfield (GB)

( * ) Notice: Subject to any disclaimer, the term of this patent is extended or adjusted under 35 U.S.C. 154(b) by 580 days.

This patent is subject to a terminal disclaimer.

(21) Appl. No.: 16/090,497

(22) PCT Filed: Mar. 29, 2017

(86) PCT No.: PCT/GB2017/050874
§ 371 (c)(1),
(2) Date: Oct. 1, 2018

(87) PCT Pub. No.: WO2017/168142
PCT Pub. Date: Oct. 5, 2017

(65) Prior Publication Data
US 2019/0110667 A1  Apr. 18, 2019

(30) Foreign Application Priority Data

Mar. 30, 2016 (GB) ....................................... 1605358
Mar. 31, 2016 (GB) ....................................... 1605435

(51) Int. Cl.
*A61B 1/00* (2006.01)
*G02B 23/24* (2006.01)

(52) U.S. Cl.
CPC ........ *A61B 1/00142* (2013.01); *A61B 1/0014* (2013.01); *A61B 1/00101* (2013.01);
(Continued)

(58) Field of Classification Search
CPC ............ A61B 1/00142; A61B 1/00144; A61B 1/00101; A61B 1/0014; A61B 1/0008;
(Continued)

(56) References Cited

U.S. PATENT DOCUMENTS 6,986,759 B1 *  1/2006  Jeremijevic ......... A61M 5/3275
                                                    604/110
2001/0053892 A1 * 12/2001 Parmigiani ....... A61M 25/0625
                                                    604/197
(Continued)

FOREIGN PATENT DOCUMENTS

JP  2007075281 A  *  3/2007
JP  2007075281 A     3/2007
(Continued)

*Primary Examiner* — Anh Tuan T Nguyen
*Assistant Examiner* — Stephen Floyd London
(74) *Attorney, Agent, or Firm* — Hayes Soloway P.C.

(57) ABSTRACT

This invention relates to a tip protector for an instrument such as an endoscope or borescope, the instrument comprising an elongate shaft having a distal tip and said tip including an end face. A tip protector device comprises a guard portion including an elongate tubular portion and a cap arranged to extend over the end face of the instrument; first and second connection members extending from the tubular portion and being movable relative to each other between a first, disengaged position in which said tip of the instrument can be inserted into and removed from the guard portion, and a second, gripping position in which the tip protector grips the shaft of the instrument, the first and second connection members being biased in the first position; and complementary engagement features on the first and second connection members configured to retain the first and second connection members in the gripping position.

19 Claims, 7 Drawing Sheets

(52) U.S. Cl.
CPC ...... *A61B 1/00144* (2013.01); *G02B 23/2476* (2013.01); *A61B 1/0008* (2013.01)

(58) Field of Classification Search
CPC ............ A61B 1/00135; A61B 1/00137; A61B 1/00062; A61B 1/00089; A61B 1/00103; A61B 1/00112; A61B 1/00121; A61B 1/00128; A61B 1/00131; G02B 23/2476; A61M 5/3202; A61M 5/3213; A61M 5/3216; A61M 39/284
USPC ........................................................ 604/192
See application file for complete search history.

(56) References Cited

U.S. PATENT DOCUMENTS

| | | | | |
|---|---|---|---|---|
| 2003/0088155 | A1* | 5/2003 | Ishibiki | A61B 1/042 600/127 |
| 2003/0190256 | A1* | 10/2003 | Halstead | A61L 2/24 422/28 |
| 2007/0212926 | A1* | 9/2007 | Nakaura | A61B 1/00089 439/465 |
| 2010/0249510 | A1* | 9/2010 | Yamada | A61B 1/00142 600/121 |
| 2013/0046138 | A1* | 2/2013 | McLawhorn | A61B 1/00089 600/104 |
| 2013/0090527 | A1* | 4/2013 | Axon | A61B 1/0008 600/114 |
| 2014/0343361 | A1* | 11/2014 | Salman | A61B 1/0014 600/125 |
| 2017/0106149 | A1* | 4/2017 | Clawson | A61M 5/3213 |
| 2017/0119234 | A1* | 5/2017 | Petroskey | A61B 1/00089 |
| 2017/0232247 | A1* | 8/2017 | Sonderegger | A61M 39/284 604/250 |
| 2019/0313889 | A1* | 10/2019 | Wassenburg | G02B 23/2476 |
| 2020/0069885 | A1* | 3/2020 | Prince | A61M 5/3219 |
| 2021/0235972 | A1* | 8/2021 | Thornton | A61B 1/00174 |

FOREIGN PATENT DOCUMENTS

| | | |
|---|---|---|
| JP | 2007313039 A | 12/2007 |
| WO | 2016059383 A2 | 4/2016 |

* cited by examiner

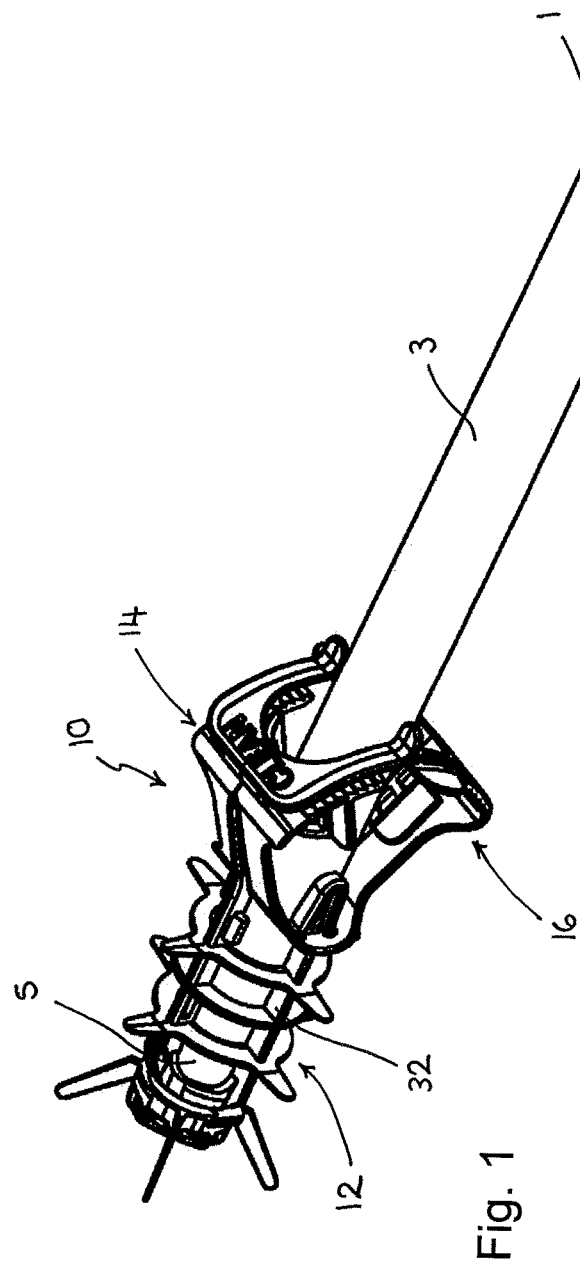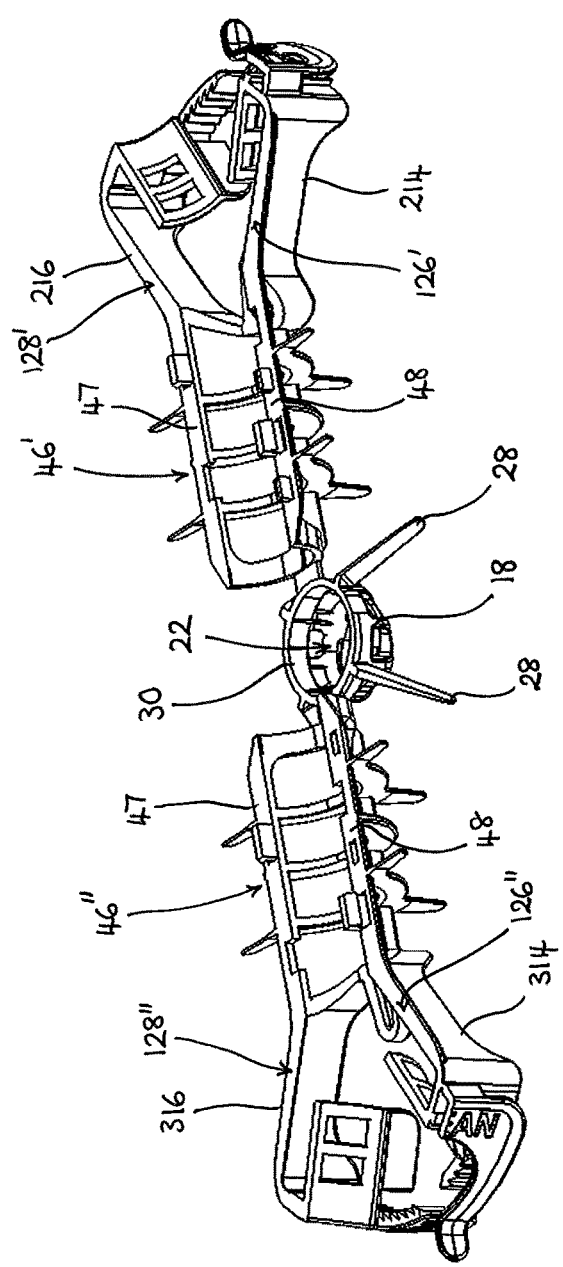

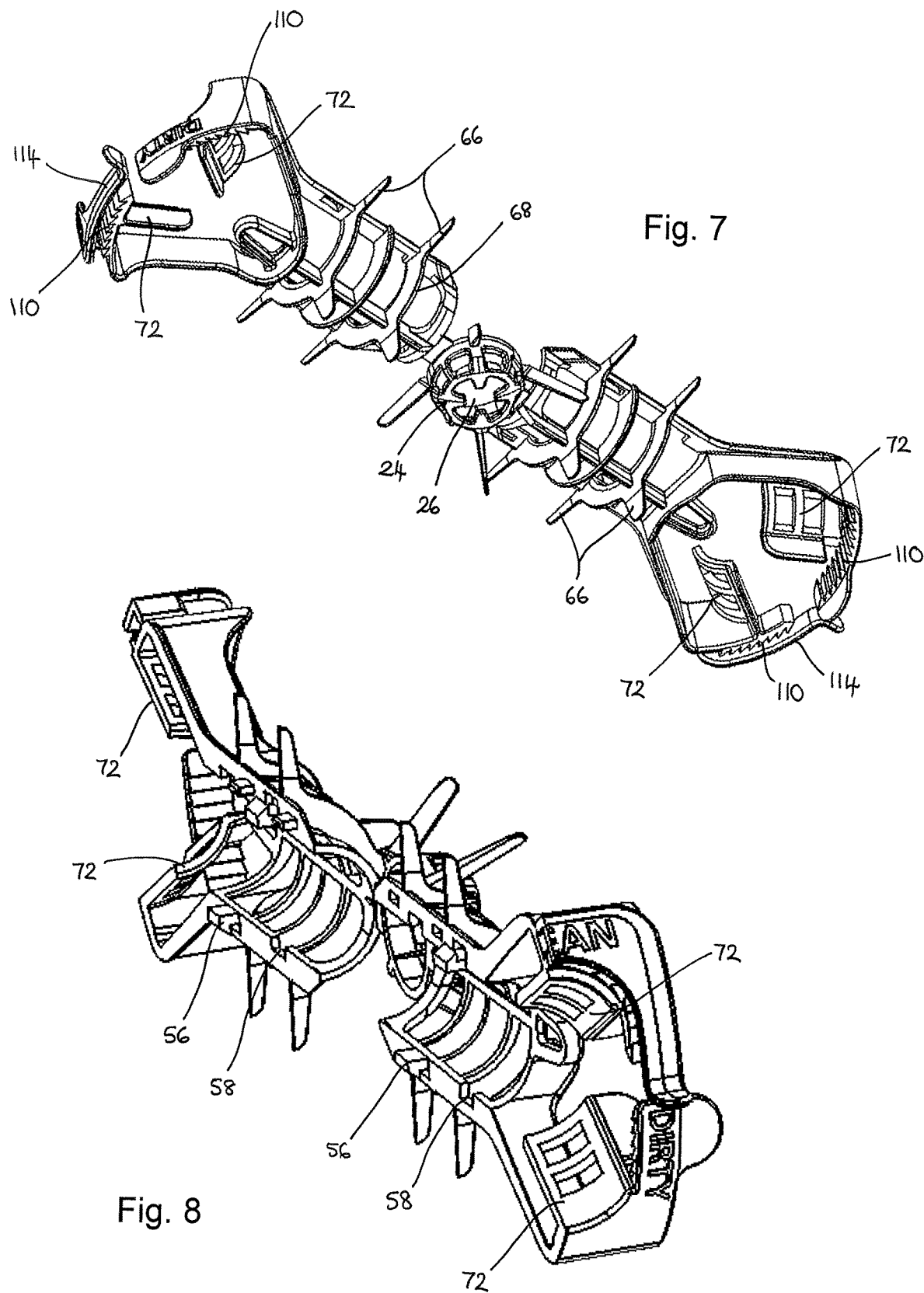

INSTRUMENT TIP PROTECTOR

CROSS-REFERENCE TO RELATED APPLICATIONS AND PRIORITY

This patent application claims priority from PCT Patent Application No. PCT/GB2017/050874 filed Mar. 29, 2017, which claims priority from UK Patent Application No. 1605358.9 filed Mar. 30, 2016 and UK Patent Application No. 1605435.5 filed Mar. 31, 2016. Each of these patent applications are herein incorporated by reference in their entirety.

BACKGROUND

This invention relates to a tip protector for an instrument such as an endoscope or borescope, to an assembly comprising a tip protector and an endoscope or borescope, and to a method of using a tip protector.

An endoscope or borescope is used to image cavities or other interior spaces that are not easily accessible and where direct observation of the space is not possible.

An endoscope or other similar elongate optical probe comprises an elongate insertion shaft having a distal tip. An objective lens is provided at the distal tip and an optical transmission system is provided within the shaft of the endoscope to transmit images from the tip to a user of the device. Typically the optical transmission system will include optical fibres and/or lens assemblies.

The shaft and tip are typically also configured to enable illumination of the area around the tip of the endoscope, and to allow other instruments to extend through the shaft and from the tip, for example biopsy forceps in the case of some medical endoscopes. Accordingly the tip of an endoscope can be very complex, very delicate and, therefore, relatively expensive.

It is thought that for every endoscope being used in a hospital setting, at least half may be unavailable for use due to repair. Damaged endoscopes can be expensive to repair, can disrupt a facility's capacity to provide endoscopy services, and can potentially compromise patient safety. Furthermore, it is believed that approximately 70% of endoscope damage may be attributed to improper handling.

During cleaning and storage of the endoscope or borescope, and additionally during sterilisation of medical endoscopes it is, therefore, desirable to protect the tip as much as possible from damage. A number of prior art devices are known, especially for use in medical applications, however, each of these devices has disadvantages.

A disadvantage of some prior art devices is the cost and complexity of manufacture. This leads to a high product unit cost, which is a significant disadvantage when these products are designed to be single use and disposable.

It is an object of the present invention to provide an improved tip protector device that overcomes at least some of the disadvantages of prior art devices.

SUMMARY OF THE INVENTION

According to a first aspect of the present invention there is provided a tip protector device for an instrument, the instrument comprising an elongate shaft having a distal tip and said tip including an end face, and the tip protector device comprising:

a guard portion engagable with said tip, the guard portion including an elongate tubular portion that, in use, extends along said shaft, the tubular portion extending between first and second ends, and a cap arranged to extend over said end face, the cap being connected to the first end of the tubular portion;

a first connection member and a second connection member, the first and second connection members extending from the second end of the tubular portion, and the first and second connection members being movable relative to each other between a first, disengaged position in which said tip of the instrument can be inserted into and removed from the guard portion, and a second, gripping position in which the tip protector grips the shaft of the instrument, the first and second connection members being biased in the first position; and complementary engagement features on each of the first and second connection members configured to engage and releasably retain the first and second connection members in the gripping position, wherein the cap is connected to the first end of the tubular portion by at least one flexible connecting member.

This design of tip protector shields and protects a significant length at the distal tip of an instrument such as an endoscope due to the inclusion of an elongate tubular guard portion. Furthermore, this design means that the tip protector grips the shaft of the instrument at a significant distance from the end face of the instrument, which minimises the likelihood of damage occurring to the tip and end face of the instrument when the tip protector is attached to and removed from the instrument.

Preferably each of the cap and the tubular member comprise at least one aperture. In particularly preferred embodiments the tubular member includes a plurality of apertures. In some embodiments the tubular member comprises a frame including a plurality of longitudinal ribs and a plurality of annular ribs. The longitudinal and annular ribs define apertures therebetween. The apertures in both the cap and the tubular member allow fluids to drain easily away from the tip of the instrument.

To reduce the complexity and cost of manufacturing such a tip protector it is advantageous if the tip protector device can be manufactured in an open configuration. To achieve this the tip protector device preferably comprises a first body portion including a first elongate channel member, a first arm and a third arm; and a second body portion including a second elongate channel member, a second arm and a fourth arm. During assembly or use of the tip protector the first and second channel members together form the tubular portion, the first and second arms together form the first connection member and the third and fourth arms together form the second connection member.

In preferred embodiments, therefore, the first and second body portions are movable between an open configuration and a closed configuration. In the closed configuration, the first and second channel members together form the tubular portion, the first and second arms together form the first connection member and the third and fourth arms together form the second connection member.

To achieve this movement between open and closed positions the first body portion is preferably connected to the cap by a first flexible connecting member and the second body portion is preferably connected to the cap by a second connecting member. The first and second connecting members may extend from diametrically opposite sides of the cap.

To retain the first and second body portions in the closed configuration, the first and second body portions preferably include latching features configured to engage with each other. The latching features may include a hook member on the first body portion and a corresponding aperture or recess on the second body portion. The aperture or recess will typically include a detent arranged to engage with the hook member to retain the first and second body portions in the closed configuration.

A tip protector device according to the invention is preferably manufactured such that a direction of movement of the first and second body portions between the open configuration and the closed configuration is transverse to a direction of movement of the first and second connection members between the disengaged position and the gripping position. In some embodiments the first and second body portions rotate about the cap between the open and closed configurations and the first and second connection members rotate about the second end of the tubular guard portion between the disengaged and gripping positions. In these embodiments the axis of rotation of the body portions is perpendicular to the axis of rotation of the connection members.

The tip protector device is preferably a unitary body. The tip protector device is also preferably made from a polymeric material. In most embodiments the tip protector device will be injection moulded.

In some embodiments an end of each of the first and second connection members furthest from the guard portion comprises two leg members. The leg members are spaced apart so as to receive the shaft of the instrument between them. In preferred embodiments the engagement features are located on the leg members.

Preferably the engagement features comprise inter-engaging teeth. The engagement features preferably include a plurality of teeth thereby allowing the tip protector to be attached to instruments of different sizes.

To assist in attaching the tip protector device to the shaft of the instrument, the first and second connection members include gripping members. In the gripping position, the gripping members are arranged to grip the shaft of the instrument. The gripping members are preferably semi-cylindrical to accommodate a substantially cylindrical instrument shaft.

To avoid cross-contamination, it is desirable if the tip protector device includes a tamper evidence feature. This feature may provide a visual indication to a user as to whether the tip protector has been previously attached to and/or removed from the same or a different instrument. This is particular important to prevent a tip protector that has previously been attached to a dirty or used instrument subsequently being attached to a clean and disinfected instrument. In preferred embodiments the tip protector comprises a tab attached to the first or the second connection member arranged to prevent disengagement of the engagement features. The tab is preferably configured such that the tab must be broken to allow the engagement features to be disengaged to move the first and second connection members to the disengaged position.

The tip protector device may also comprise distinguishing features. For example, a first distinguishing feature may be provided on the tab and a second distinguishing feature may be concealed by the tab when the first and second connection members are in the gripping position. In these embodiments the second distinguishing feature is preferably revealed when the tab is broken, thereby providing a visual indication to a user as to the status of the instrument to which the tip protector is attached. The distinguishing features may, for example, indicate whether the instrument is used or clean.

To provide additional protection to the tip of the instrument, especially against knocks, the guard portion of the tip protector device preferably comprises a plurality of spurs extending outwardly from one or both of the cap and the tubular portion. The spurs may be made of a resilient material.

Preferably the tip protector comprises or is made of a first, harder polymeric material and a second, softer polymeric material.

According to a second aspect of the present invention, there is provided an assembly comprising a tip protector device according to the first aspect of the invention and an instrument, the instrument comprising an elongate shaft having a tip and said tip including an end face, and the tip protector device being engaged with the tip of the instrument. The instrument will typically be an endoscope.

According to a third aspect of the present invention, there is provided a method of using a tip protector device to protect a distal tip of an instrument, the method comprising:
 inserting the distal tip of the instrument into an elongate tubular guard portion of the tip protector device until an end face of the distal tip is seated in a cap portion of the tip protector device, the cap portion being connected to a first end of the tubular guard portion;
 moving a first connection member and a second connection member of the tip protector device from a disengaged position to a gripping position in which the tip protector grips a shaft of the instrument, the first and second connection members extending from a second end of the elongate tubular guard portion and the first and second connection members being biased in the disengaged position; and engaging complementary engagement features on each of the first and second connection members to releasably retain the first and second connection members in the gripping position.

The method preferably further comprises moving the first and second connection members towards each other until a first gripping member of the first connection member and a second gripping member of the second connection member grip the shaft of the instrument.

In some embodiments the tip protector device comprises a first body portion including a first elongate channel member, a first arm and a third arm, and a second body portion including a second elongate channel member, a second arm and a fourth arm, the first and second body portions being hingedly connected to the cap portion. In these embodiments the method preferably comprises moving the first and second body portions from an open configuration in which the first and second body portions extend in opposite directions from the cap portion to a closed configuration in which the first and second body portions are in touching contact and the first and second channel members together form the tubular guard portion, the first and second arms together form the first connection member and the third and fourth arms together form the second connection member. A direction of movement of the first and second body portions between the open configuration and the closed configuration is preferably transverse to a direction of movement of the first and second connection members between the disengaged position and the gripping position. In particularly preferred embodiments the method further comprises engaging latching features on the first and second body portions to retain the first and second body portions in the closed configuration.

To avoid cross-contamination, it is desirable if the tip protector device includes a tamper evidence feature. In these embodiments the method may further comprise breaking a tab attached to the first connection member to permit disengagement of the engagement features, and moving the first and second connection members to the disengaged position.

BRIEF DESCRIPTION OF THE DRAWINGS

The invention will now be further described by way of example only and with reference to the accompanying drawings, in which:

FIG. 1 shows a tip protector according to the present invention in a closed configuration around a tip of an instrument;

FIG. 2 is a perspective view of the tip protector of FIG. 1 in an open configuration;

FIG. 7 is a perspective view of the tip protector of FIG. 1 in an open configuration;

FIG. 8 is a perspective view from an end of the tip protector of FIG. 1, with the tip protector in an open configuration;

DETAILED DESCRIPTION

Figure 3:
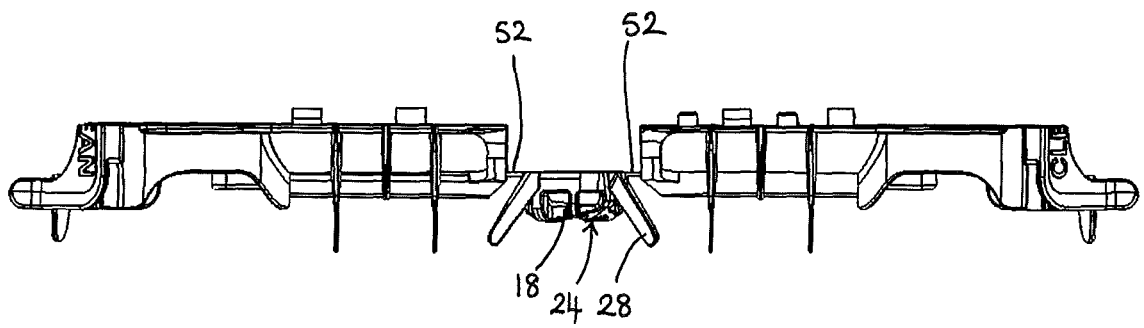
FIG. 3 is a side view of the tip protector of FIG. 1 in an open configuration.
Figure 4:
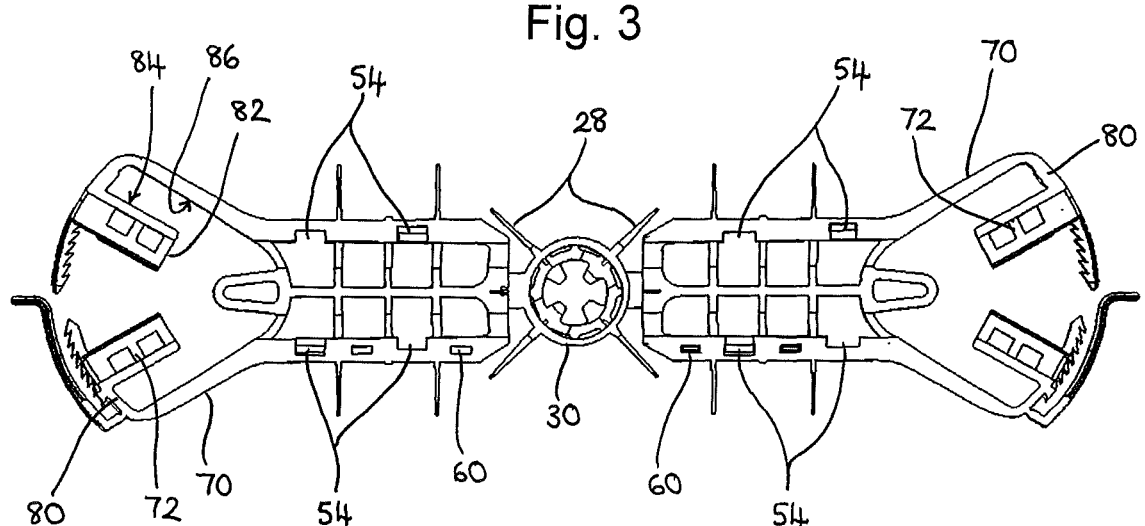
FIG. 4 is a top view of the tip protector of FIG. 1 in an open configuration.
Figure 5:
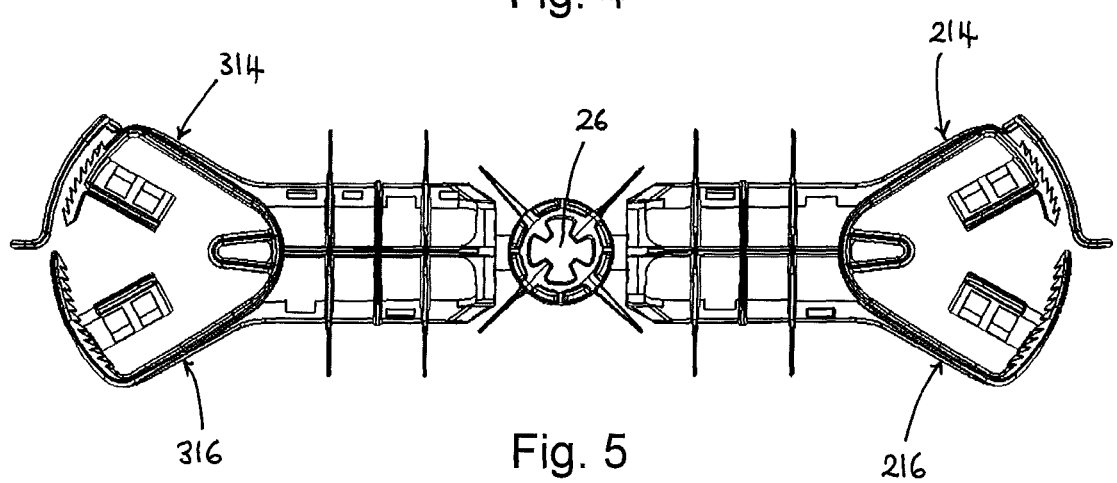
FIG. 5 is an underside view of the tip protector of FIG. 1 in an open configuration.
Figure 6:
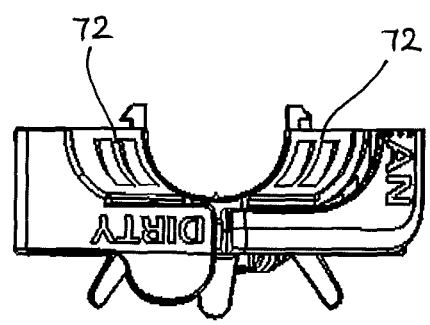
FIG. 6 is an end view of the tip protector of FIG. 1 in an open configuration.

The present invention concerns a device for protecting the distal tip of an endoscope or similar instrument. By similar instrument it is meant any instrument having an elongate shaft and a distal tip where it would be desirable or beneficial to protect the tip from damage. Typically these instruments will be optical instruments having a lens or part of a lens system at the distal tip. Such instruments may be, but are not limited to, borescopes such as those used in industrial applications or endoscopes such as those used in medical applications. Endoscopes may include scopes such as colonoscopes, gastroscopes, esophagoscopes and sigmoidoscopes. It will be understood that references in the following description to an endoscope also encompasses a borescope and similar instruments.

An endoscope 1 includes an elongate shaft or insertion tube 3 having a distal tip 5. The shaft or insertion tube 3 may be flexible or rigid, depending on the specific application. Typically the distal tip 5 of the endoscope 1 will include an end face that is planar and is substantially perpendicular to a longitudinal axis of the shaft 3; however, in some endoscopes the end face may be curved, or the tip may be tapered such that the end face is at an angle of less than 90° to the longitudinal axis.

The tip protector devices of the present invention are configured to engage with and attach to the tip 5 or shaft 3 of the endoscope 1 so as to protect the tip 5 and, in particular, to protect the end face of the tip 5 from potential damage.

An embodiment of a tip protector 10 according to the invention comprises a guard portion 12, a first connection member 14 and a second connection member 16. As shown in FIG. 1, the guard portion 12 extends around and over the tip of the endoscope 1, and the first and second connection members 14, 16 engage with each other to retain the tip protector 10 on the endoscope 1.

Figure 9:
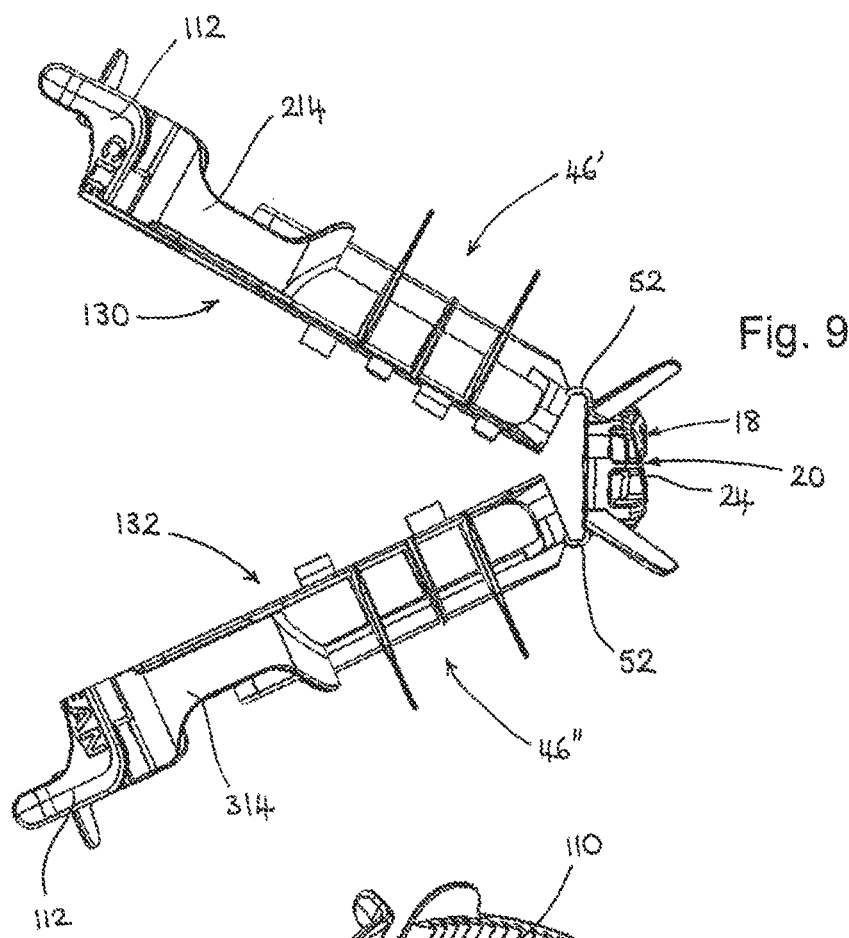
FIG. 9 is a side view of the tip protector of FIG. 1 showing the tip protector in a partially closed configuration.
Figure 10:
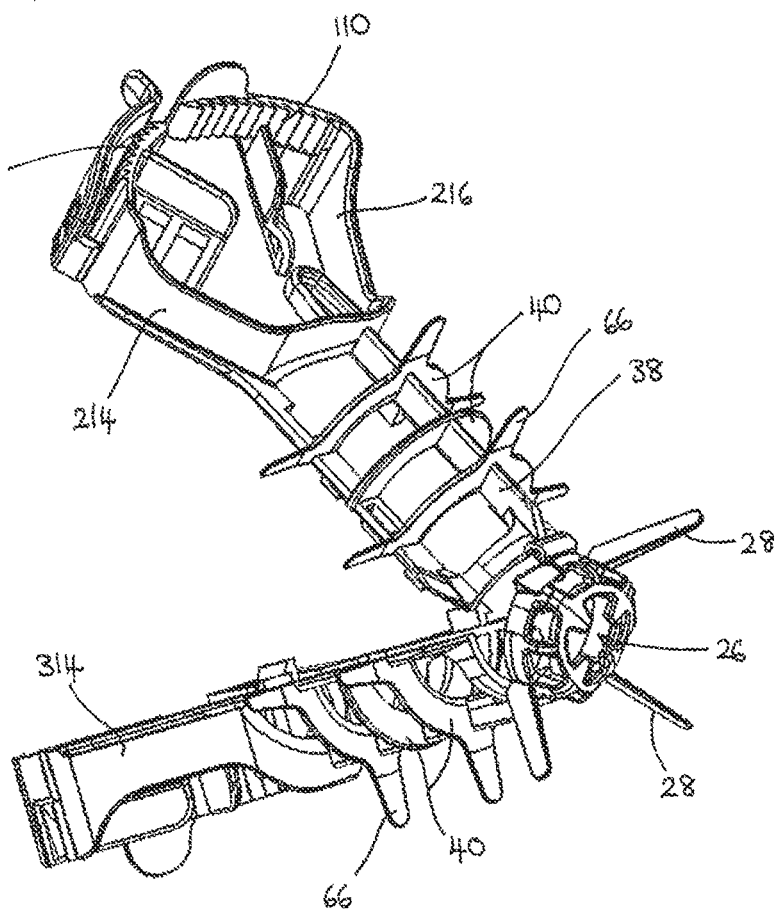
FIG. 10 is a perspective view from a first end of the tip protector of FIG. 1 showing the tip protector in a partially closed configuration.
Figure 11:
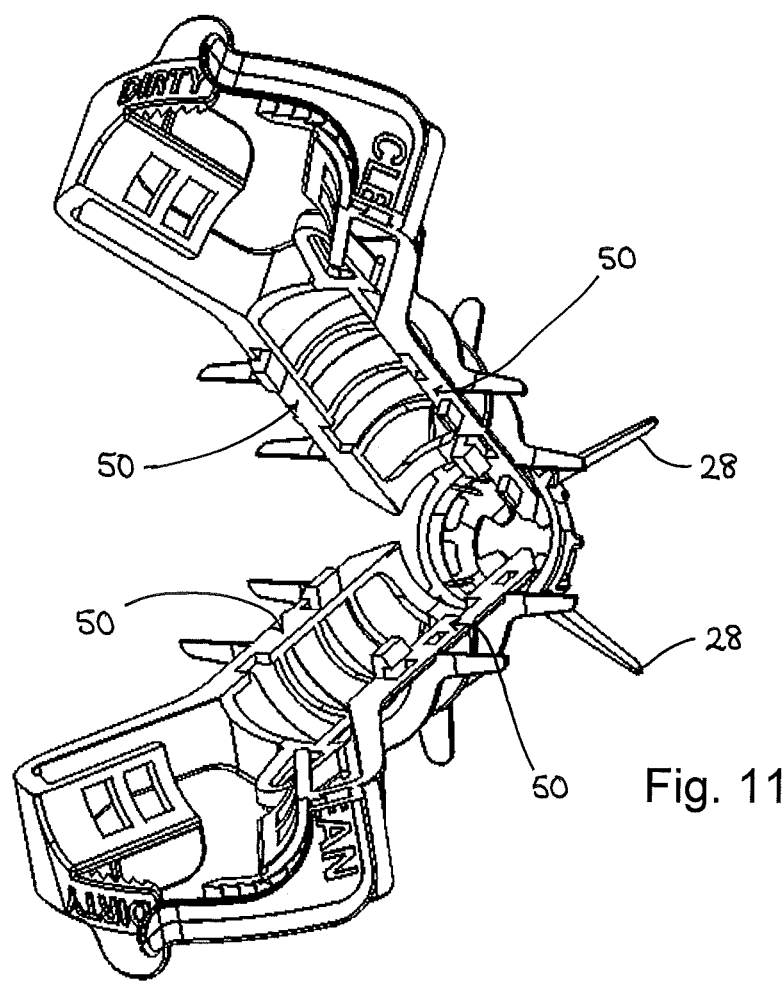
FIG. 11 is a perspective view from a second end of the tip protector of FIG. 1 showing the tip protector in a partially closed configuration.
Figure 12:
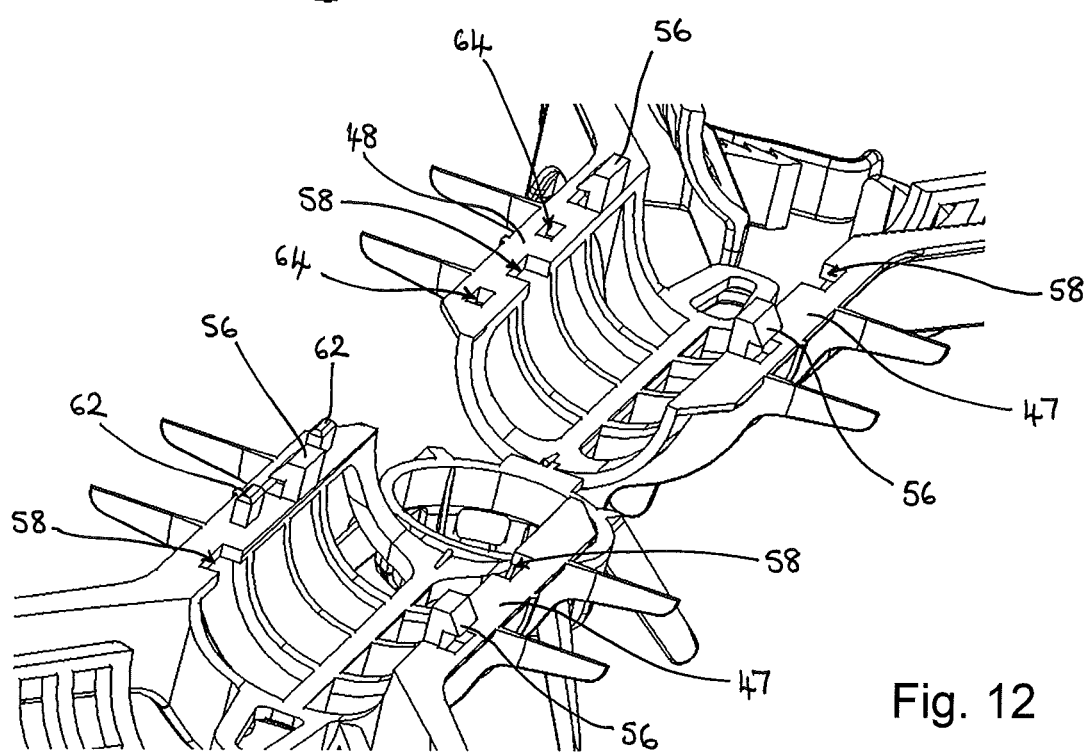
FIG. 12 is a perspective view of a part of the tip protector of FIG. 1 in an open configuration showing a latch mechanism used to retain the tip protector in the closed configuration.
Figure 13:
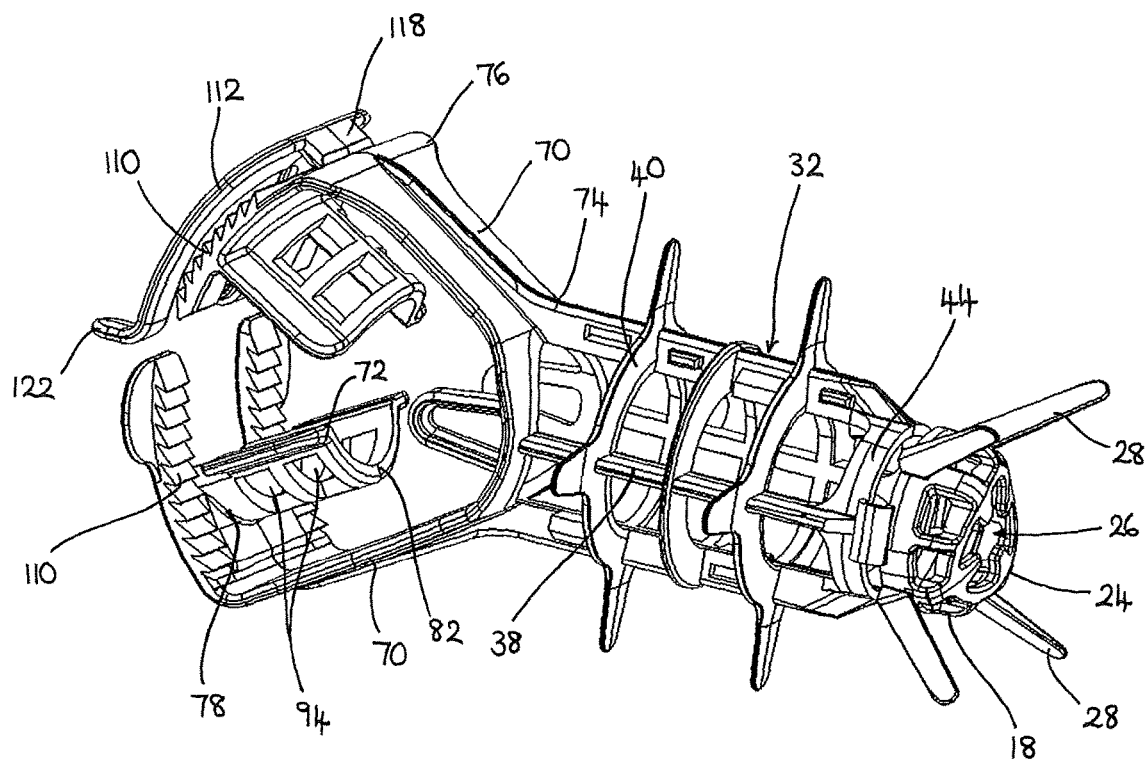
FIG. 13 is a perspective view of the tip protector of FIG. 1 in a closed configuration.
Figure 14:
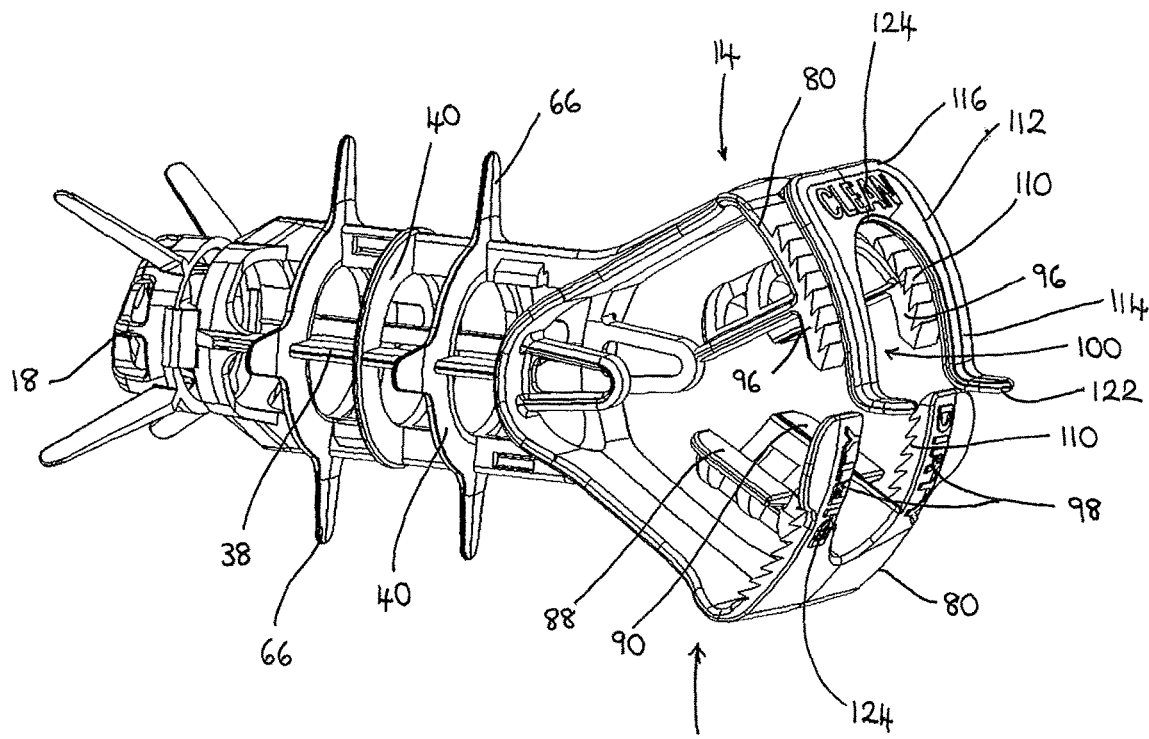
FIG. 14 is another perspective view of the tip protector of FIG. 1 in a closed configuration.
Figure 15:
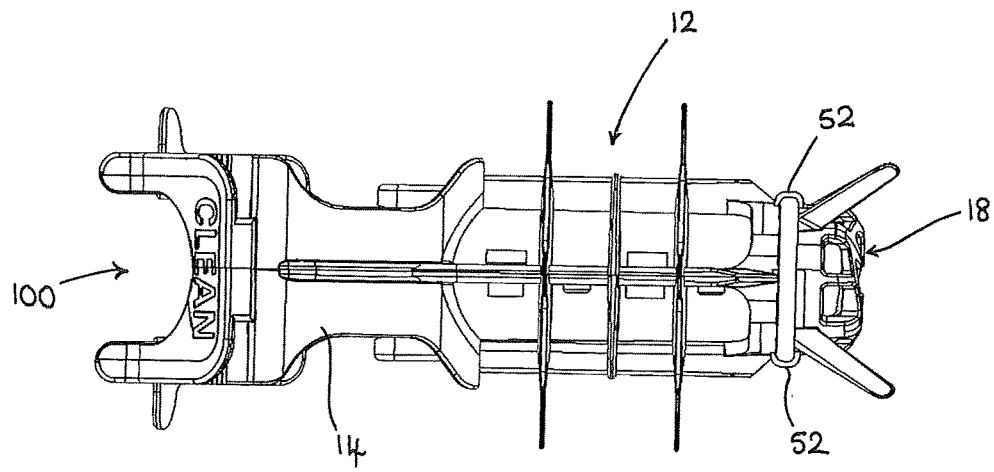
FIG. 15 is a first side view of the tip protector of FIG. 1 in a closed configuration.
Figure 16:
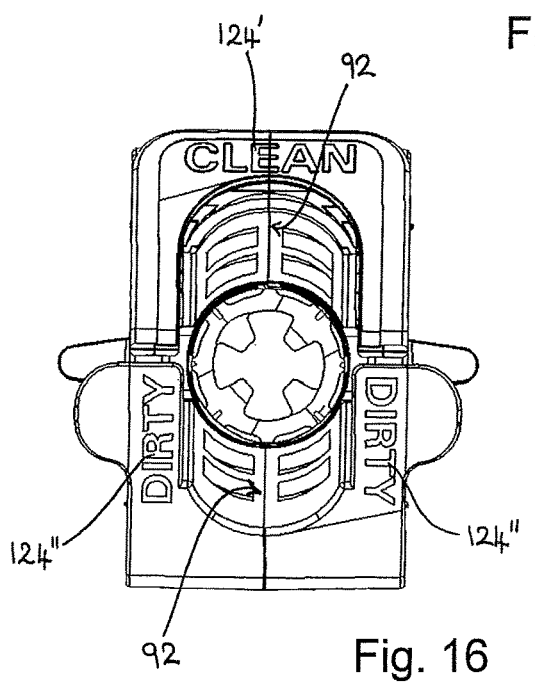
FIG. 16 is a view from a second end of the tip protector of FIG. 1, with the tip protector in a closed configuration.
Figure 17:
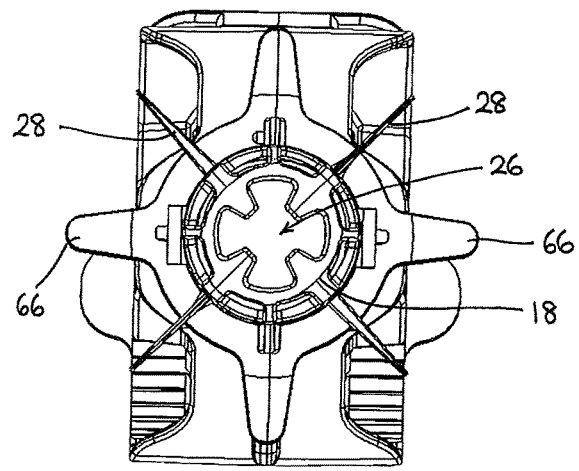
FIG. 17 is a view from a first end of the tip protector of FIG. 1, with the tip protector in a closed configuration.
Figure 18:
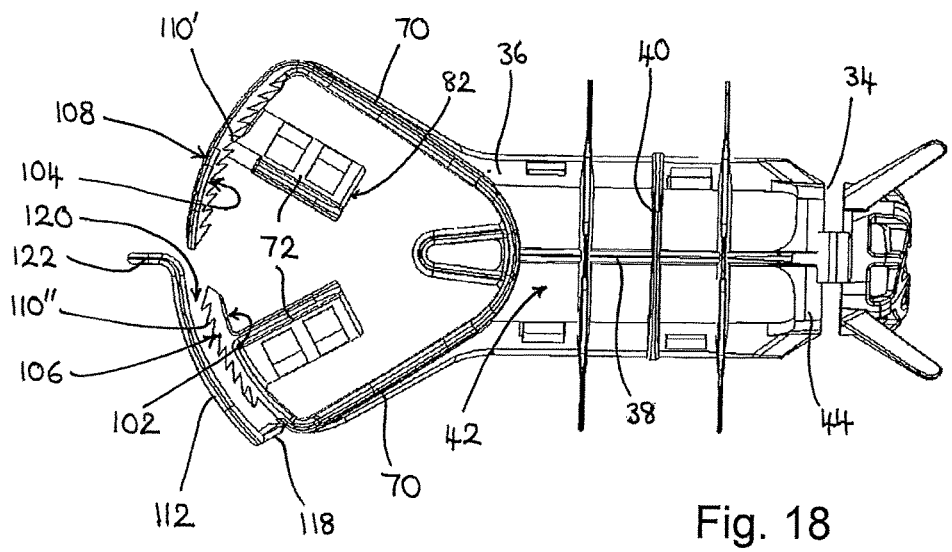
FIG. 18 is a second side view of the tip protector of FIG. 1, perpendicular to the view of FIG. 15, with the tip protector in a closed configuration.

The tip protector 10 is manufactured in a first, open configuration as shown in FIGS. 2 to 8. Typically the tip protector 10 will be moulded from a suitable polymeric material. Preferably the tip protector 10 is injection moulded. In use, the tip protector 10 is folded into a closed configuration, as illustrated in FIGS. 9 and 10. Once in the closed configuration, shown in FIGS. 11 to 16, the first and second connection members 14, 16 may be engaged to secure the tip protector 10 to an endoscope 1. The tip 5 of the endoscope 1 may be inserted into the tip protector 10 after the tip protector 10 has been formed into the closed configuration or, alternatively, the tip protector 10 may be folded into the closed configuration around the tip 5 of the endoscope 1.

The guard portion 12 comprises a generally circular cover plate or cap 18. The cap 18 is curved or dish-shaped and has a first, convex surface 20 and a second, concave surface 22. When an endoscope tip 5 is located in the tip protector 10, the cap 18 extends across the end face of the tip 5 such that the cap 18 protects the end face from damage that may occur during transportation or storage of the endoscope 1. A central region or nose 24 of the cap 18 includes an aperture 26 that, in use, allows liquids such as water to easily drain away from the tip 5.

A plurality of spurs 28 extend outwardly from an annular edge region 30 of the cap 18. In this example four spurs 28 extend outwardly and in a direction generally towards the nose 24 of the cap 18. A length of the spurs 28 is preferably such that the spurs 28 extend or protrude beyond the nose 24 of the cap 18. The spurs 28 act to protect the cap 18 and, therefore, the tip 5 of the endoscope 1 from knocks.

The guard portion 12 further comprises a tubular sleeve or protective frame 32 that, in use, extends around the shaft 3 of the endoscope 1 proximate the tip 5. The frame 32 is elongate such that a length of the frame 32 between first and second ends 34, 36 is greater than a diameter of the frame 32. The frame 32 comprises a plurality of longitudinal ribs 38 extending between the first and second ends 34, 36 and a plurality of annular ribs 40. Each of the annular ribs 40 intersects the longitudinal ribs 38 substantially perpendicularly to the longitudinal ribs 38. The longitudinal and annular ribs 38, 40 together define a cylindrical bore 42 of the frame 32 within which the shaft 3 of the endoscope 1 is received. An annular cuff 44 is located at the first end 34 of the frame 32. The annular cuff 44 has substantially the same internal diameter as the annular edge region 30 of the cap 18. An internal diameter of each of the annular ribs 40 is preferably greater than the internal diameter of the cuff 44.

The frame 32 is formed from two channel members 46', 46". Each channel member 46', 46" has a semi-annular cross-sectional shape perpendicular to a longitudinal axis. In this way, each of the channel members has a half-pipe shape terminating in first and second longitudinal edge members 47, 48, providing mating surfaces 50. Each channel member 46', 46" includes at least one complete longitudinal rib 38, a portion of each of the annular ribs 40 and a portion of the cuff 44. Typically each channel member 46', 46" will include half of each of the annular ribs 40 and half of the cuff 44.

Each of the channel members 46', 46" is connected to the cap 18 by means of a bendable connecting member 52 extending between the annular edge region 30 of the cap 18 and the respective portion of the cuff 44 at the first end 34 of the channel member 46', 46". The connecting member 52 may comprise a strap or a live hinge. The connecting members 52 extend from diametrically opposite sides of the cap 18 and permit movement of the channel members 46', 46" between the open configuration in which first and second channel members 46', 46" extend in opposite directions away from each other and the closed configuration in which the mating surfaces 50 of the first longitudinal edge members 47 of the first and second channel members 46', 46" and the mating surfaces 50 of the second longitudinal edge members 48 of the first and second channel members 46', 46" are in contact. In the closed configuration, therefore, the channel members 46', 46" form the tubular frame 32, and the first longitudinal edge members 47 of the first and second channel members 46', 46" form a first longitudinal rib 38 and the second longitudinal edge members 48 of the first and second channel members 46', 46" form a second longitudinal rib 38.

To retain the channel members 46', 46" in the closed configuration, complementary latching features 54 are provided on each of the first longitudinal edge members 47 and each of the second longitudinal edge members 48. The latching features include a hook member 56 on a first one of the longitudinal edge members and a complementary aperture 58 on another one of the longitudinal edge members. Preferably a detent surface is associated with the aperture and, in the closed configuration, the hook member 56 is arranged to extend through the aperture 58 and engage with the detent surface.

Alignment features 60 may also be provided on the first and/or the second longitudinal edge members 47, 48. The alignment features 60 may include a projection or post 62 on one of the longitudinal edge members and a hole or recess 64 arranged to receive the post 62 on another one of the longitudinal edge members.

A plurality of spurs 66 extend radially outwardly from the tubular frame 32. In this embodiment the spurs 66 extend from an outer edge 68 of at least one of the annular ribs 40. The spurs 66 act to protect the tubular frame 32 and, therefore, the shaft 3 and tip 5 of the endoscope 1 from knocks.

The first and second connection members 14, 16 extend from the second end 36 of the tubular frame 32 in a direction substantially away from the first end 34 of the frame 32. The first and second connection members 14, 16 are movable between a disengaged position, in which the endoscope tip 5 may be inserted into and removed from the tip protector 10, and an engaged or gripping position, in which the first and second connection members 14, 16 grip the shaft 3 of the endoscope 1 to retain the tip protector 10 on the endoscope 1. Preferably the first and second connection members 14, 16 are biased in the disengaged position.

Each of the first and second connection members 14, 16 includes an outer wall portion 70 and an inner collar portion 72. A first end 74 of the wall portion 70 is connected to the second end 36 of the tubular frame 32, and an opposing second end 76 of the wall portion 70 is connected to a respective second end 78 of the collar portion 72 by means of a bridging portion 80. The collar portion 72 extends from its second end 78 in a direction substantially towards the guard portion 12 and a first end 82 of the collar portion 72 is a free end 82. The connection between the wall portion 70 and the collar portion 72 is such that a space is defined between an outer surface 84 of the collar portion 72 and an inner surface 86 of the wall portion 70.

Each of the collar portions 72 has a semi-annular cross-sectional shape perpendicular to an axis extending between the first and second ends 82, 78 of the collar portion 72. In this way, each of the collar portions 72 has a half-pipe shape terminating in first and second longitudinal side edges 88, 90, which in this embodiment are substantially parallel to each other. The outer surface 84 of the collar portion 72 has a convex curvature and an inner surface 92 has a concave curvature. In this embodiment of the protector device 10, the collar portion 72 is elongate such that a length of the collar portion 72 between the first and second ends 82, 78 is greater than the diameter of the collar portion 72, i.e. the distance between the first and second side edges 88, 90.

Furthermore, the collar portions 72 include a plurality of holes 94 which aid air flow around the shaft 3 or tip 5 of the endoscope 1 and permit liquid to drain more easily from the shaft 3 and tip 5 of the endoscope 1.

An end of each of the connection members 14, 16 furthest from the guard portion 12 comprises a pair of leg members 96, 98. The leg members of each pair 96, 98 extend parallel to each other and are spaced apart so as to receive the shaft 3 of the endoscope 1 between them. In particular, the first connection member 14 of the device 10 comprises a first pair of legs 96 that extend from the bridging portion 80 in a direction substantially towards the second connection member 16, and the second connection member 16 comprises a second pair of legs 98 that extend from the bridging portion 80 in a direction substantially towards the first connection member 14. The legs 96, 98 extend from the respective bridging portion 80 proximate the side edges 88, 90 of the collar portion 72 such that a gap 100 is defined between the legs 96, 98 and the distance between the legs 96, 98 is substantially equal to the internal diameter of the collar portion 72.

Each of the legs 96, 98 has a first surface 102, 104 facing in a direction substantially towards the guard portion 12, and an opposing second surface 106, 108 facing in a direction substantially away from the guard portion 12. A first engagement feature is provided on the first pair of legs 96 and is arranged to engage with a second engagement feature provided on the second pair of legs 98. In this embodiment the engagement features comprise complementary teeth 110 having a sawtooth profile that engage to retain the tip protector 10 in the engaged or gripping configuration. In particular a first toothed surface 110' is provided on the second surface 104 of the first pair of legs 96 and a second toothed surface 110" is provided on the first surface 106 of the second pair of legs 98.

In use, the connection members 14, 16 are moved towards each other, to move the tip protector 10 from a disengaged position to a gripping position. During this movement, as the first and second pairs of legs 96, 98 overlap each other, the sawtooth profile of the teeth 110 is such that the teeth 110 on each of the connection members 14, 16 are able to slide over each other. When the force is removed from the connection members 14, 16, the teeth 110 engage or latch together so that the tip protector 10 is retained in the gripping position.

By providing a plurality of teeth 110 on each of the connection members 14, 16 the connection members 14, 16 can be pressed together until the collar portions 72 grip the shaft 3 of the endoscope 1. The teeth 110 will then engage to retain the connection members 14, 16 in this position. In this way, the tip protector 10 is able to accommodate different sizes of shaft 3.

The tip protector 10 further comprises a tab 112 attached to the first connection member 14. The tab 112 comprises two leg portions 114 that are joined together at a first end 116 of the tab 112. The tab 112 is attached to the bridging portion 80 of the connection member 14 at its first end 116 by a spacing element 118 such that the leg portions 114 extend over the legs 96 of the connection member 14. The connection between the tab 112 and the connection member 14, and in particular a size of the spacing element 118, is such that a gap 120 is defined between the leg portions 114 of the tab 112 and the legs 96 of the connection member 14. The gap 120 is sized to receive the legs 98 of the second connection member 16 when the tip protector 10 is moved into the gripping position.

The leg portions 114 of the tab 112 extend beyond the legs 96 of the connection member 14 and each end of the leg portions 114 comprises a gripping lug 122. Each gripping lug 122 extends substantially perpendicularly from the tab 112 in a direction away from the connection member 14 to allow a user to grip the lug 122 and break the tab 112.

The location of the tab 112 is such that the tab 112 conceals the engagement features when the first and second connection members 14, 16 are in the gripping position. Furthermore, the position of the tab 112, and in particular the leg portions 114 of the tab 112, means that the connection members 14, 16 cannot be moved with respect to each other to disengage the inter-engaged teeth 110. To allow the engagement features to be disengaged the tab 112 must be broken by pulling on the lugs 122 to move the leg portions 114 away from the legs 96 of the connection member 14. Pulling on the lugs 122 in this way at least partially breaks the attachment of the tab 112 to the connection member 14.

In preferred embodiments the attachment of the tab 112 to the connection member 14 is such that the tab 112 remains connected to the connection member 14 after the tab 112 has been broken. This may be achieved by providing a line of weakness in the spacing element 118. The spacing element 118 supports the tab 112 in a fixed position relative to the connection member 14 until a user pulls on the lugs 122 with sufficient force as to break the spacing element 118 along the line of weakness. The line of weakness, however, does not extend through the full width or thickness of the spacing element 118 so that the spacing element 118 becomes a live hinge after the tab 112 has been broken. In other embodiments the spacing element may be a live hinge and an additional support element may be provided that supports the tab in a fixed position during use of the tip protector and which is then broken when a user applies sufficient force to the lugs. Once the tab 112 has been broken the first and second connection members 14, 16 can then be moved relative to each other to disengage the complementary teeth 110 and return the device 10 to the closed and disengaged position.

The tip protector 10 preferably comprises distinguishing features 124. The distinguishing features 124 are provided to allow a user to determine whether the tip protector 10 has been engaged with a clean and/or a dirty endoscope. For example, the tip protector 10 may be attached to a clean endoscope after sterilisation with a first distinguishing feature 124' being displayed. When the endoscope 1 is to be used in a medical procedure, the tip protector 10 is removed and in doing so a second distinguishing feature 124" is displayed. The tip protector 10 can then be placed back on the used, dirty endoscope 1 with the second distinguishing feature 124" displayed. The distinguishing features 124 are configured such that the second distinguishing feature 124" displays to a user that the tip protector 10 has been used on a dirty endoscope and should not be subsequently placed on a clean endoscope.

In this embodiment a first distinguishing feature 124' is provided on the tab 112 attached to the first connection member 14 and a second distinguishing feature 124" is provided on the second connection member 16. The first and second distinguishing features 124', 124" are sufficiently different to allow them to be quickly and easily distinguished.

The position of the second distinguishing feature 124" is such that the second distinguishing feature 124" is concealed by the tab 112 when the first and second connection members 14, 16 are in the gripping position. When the tab 112 is broken the second distinguishing feature 124" is then revealed.

The first distinguishing feature 124' may comprise the word CLEAN and the second distinguishing feature 124" may comprise the word DIRTY. In other embodiments the distinguishing features 124 may comprise any other suitable symbols, letters, numbers or other graphical devices. For example, the first distinguishing feature may comprise an area having a first colour such as green and the second distinguishing feature may comprise an area having a second colour such as red.

The first connection member 14 is formed from first and second portions or arms 214, 314 and the second connection member 16 is formed from third and fourth portions or arms 216, 316. Each of the first and second arms 214, 314 includes part of the wall portion 70, the collar portion 72 and the bridging portion 80 of the first connection member 14 and each of the third and fourth arms 216, 316 includes part of the wall portion 70, the collar portion 72 and the bridging portion 80 of the second connection member 16. Furthermore, each of the first and second arms 214, 314 includes one of the legs 96 and each of the third and fourth arms 216, 316 includes one of the legs 98. In this embodiment, each of the first and second arms 214, 314 also includes a part of the tab 112 and in particular each of the arms 214, 314 includes one of the two leg portions 114.

The first and third arms 214, 216 extend from the second end 36 of the first channel member 46' and the second and fourth arms 314, 316 extend from the second end 36 of the second channel member 46".

In this way, the tip protector 10 comprises a first body portion 130 and a second body portion 132. The first body portion 130 includes the first channel member 46', the first arm portion 214 and the third arm portion 216. The second body portion 132 includes the second channel member 46", the second arm portion 314 and the fourth arm portion 316.

The tip protector 10 may be made from two different polymeric materials. In particular, a first part of the tip protector 10 may be moulded from a first, harder polymer and a second part of the tip protector 10 may be moulded from a second, softer polymer. In preferred embodiments the first and second connection members 14, 16 may comprise the harder polymer and the guard portion 12 may comprise the softer polymer. In particularly preferred embodiments the spurs 28, 66 are made of the softer polymeric material and the first and second pairs of legs 96, 98 and the teeth 110 are made of the harder polymeric material. In some embodiments the harder polymer material may be overmoulded with the softer polymer material such that an outer layer, including the spurs 28, 66, of the tip protector 10 is formed from the softer polymer material thereby providing impact resistance. The harder polymer is preferably a rigid polymeric material such as a polyethylene or a polypropylene polymer and the softer polymer is preferably an elastomer such as rubber, polyurethane or silicone. The harder polymeric materials will typically have a Shore D hardness of greater than 25 or greater than 30. The softer polymeric materials will typically have a Shore A hardness of between 50 and 70 and more preferably between 60 and 70.

A tip protector according to the present invention is manufactured in the open configuration. Typically the tip protector will also be transported and stored in this configuration before use.

When a user wishes to attach a tip protector to an instrument such as an endoscope, a user will move the tip protector into the closed configuration by bending the connecting members to bring the first and second body portions into contact with each other. To retain the tip protector in the closed configuration the user engages the latching features.

When the tip protector 10 is moved from the open configuration to the closed configuration, a mating surface 126' of the first arm 214 locates adjacent a mating surface 126" of the second arm 314. Preferably the mating surface 126' of the first arm 214 is in touching contact with the mating surface 126" of the second arm 314 when the tip protector 10 is in the closed configuration. Similarly, when the tip protector 10 is moved from the open configuration to the closed configuration, a mating surface 128' of the third arm 216 locates adjacent a mating surface 128" of the fourth arm 316. Preferably the mating surface 128' of the third arm 216 is in touching contact with the mating surface 128" of the fourth arm 316 when the tip protector 10 is in the closed configuration.

With the tip protector in the closed configuration a tip of an endoscope can be inserted into the bore of the guard portion. Typically the tip will be inserted so that the end face of the tip is seated in the cap of the tip protector.

The user then moves the first and second members in a direction towards each other from the disengaged position to the gripping position. The first and second members are pressed together until the collar portions grip the shaft of the endoscope. The engagement features on the first and second connection members then engage to retain the tip protector in the gripping position. Typically the tip protector is used for the first time to cover the tip of a clean endoscope. Accordingly, the first distinguishing feature on the tab will be visible to the user which indicates that the endoscope is clean and ready for use.

To use the endoscope, the tab is broken to allow a user to disengage the connection members and return the connection members to the disengaged position. In this position the endoscope tip can be removed from the guard portion with the tip protector still in the closed configuration.

After the endoscope has been used, the tip can be re-inserted into the guard portion, and the first and second members can be pressed together to move them from the disengaged position to the gripping position. Because the tab is broken the second distinguishing feature is visible to the user which indicates that the endoscope is used and requires cleaning and disinfection.

When the tip protector is removed from the used endoscope it is disposed of and a new tip protector is then attached to the cleaned endoscope ready for use again.

The present invention, therefore, provides a tip protector device that is easy and cost effective to manufacture, as well as being easy to attach to the tip of an instrument such as an endoscope.

The invention claimed is:

1. A tip protector device for an instrument, the instrument comprising an elongate shaft having a distal tip and said tip including an end face, and the tip protector device comprising:
   a guard portion configured to engage with said tip, the guard portion including an elongate tubular portion configured to extend along said shaft, the tubular portion extending between first and second ends, and a cap configured to extend over said end face, the cap being connected to the first end of the tubular portion;
   a first connection member including a first gripping member and a second connection member including a second gripping member, the first and second connection members extending from the second end of the tubular portion in a direction away from the first end of the tubular portion, and the first and second connection members movable relative to each other between a first, disengaged position in which the guard portion is configured to permit insertion and removal of said tip of the instrument, and a second, gripping position in which the gripping members are configured to grip the shaft of the instrument, the first and second connection members being biased in the first position; and
   complementary engagement features on each of the first and second connection members configured to engage and releasably retain the first and second connection members in the gripping position,
   wherein the cap is connected to the first end of the tubular portion by at least one flexible connecting member.

2. The tip protector device of claim 1, wherein each of the cap and the tubular portion comprises at least one aperture.

3. The tip protector device of claim 1, wherein the tubular portion comprises a frame including a plurality of longitudinal ribs and a plurality of annular ribs.

4. The tip protector device of claim 1, the device comprising:
   a first body portion including a first elongate channel member, a first arm and a third arm; and
   a second body portion including a second elongate channel member, a second arm and a fourth arm,
   wherein the first and second channel members together form the tubular portion, the first and second arms together form the first connection member and the third and fourth arms together form the second connection member.

5. The tip protector device of claim 4, wherein the first body portion is connected to the cap by a first flexible connecting member of the at least one flexible connecting member and the second body portion is connected to the cap by a second flexible connecting member of the least one flexible connecting member.

6. The tip protector device of claim 5, wherein the first and second flexible connecting members extend from diametrically opposite sides of the cap.

7. The tip protector device of claim 4, wherein the first and second body portions are movable between an open configuration and a closed configuration and wherein, in the closed configuration, the first and second channel members together form the tubular portion, the first and second arms together form the first connection member and the third and fourth arms together form the second connection member.

8. The tip protector device of claim 7, wherein the first and second body portions include latching features configured to engage and retain the first and second body portions in the closed configuration.

9. The tip protector device of claim 7, wherein a direction of movement of the first and second body portions between the open configuration and the closed configuration is transverse to a direction of movement of the first and second connection members between the disengaged position and the gripping position.

10. The tip protector device of claim 1, wherein the tip protector device is made from a polymeric material.

11. The tip protector device of claim 1, wherein an end of each of the first and second connection members furthest from the guard portion comprises two leg members, the leg members being spaced apart and configured to receive the shaft of the instrument between them.

12. The tip protector device of claim 11, wherein the engagement features are located on the leg members.

13. The tip protector device of claim 1 wherein the engagement features comprise inter-engaging teeth.

14. The tip protector device of claim 1 further comprising a tab attached to the first or the second connection member, the tab arranged to prevent disengagement of the engagement features, and the tab being configured such that the tab must be broken to allow the engagement features to be disengaged to move the first and second connection members to the disengaged position.

15. The tip protector device of claim 14 further comprising distinguishing features, a first distinguishing feature being provided on the tab and a second distinguishing feature being concealed by the tab when the first and second connection members are in the gripping position, the second distinguishing feature being revealed when the tab is broken.

16. The tip protector device of claim 1, wherein the guard portion comprises a plurality of spurs extending outwardly from one or both of the cap and the tubular portion.

17. The tip protector device of claim 1 comprising a first, harder polymeric material and a second, softer polymeric material.

18. An assembly comprising:
the tip protector device of claim 1; and
an instrument, the instrument comprising an elongate shaft having a tip and said tip including an end face, and the tip protector device being engaged with the tip of the instrument.

19. The assembly of claim 18, wherein the instrument is an endoscope.

* * * * *